US010376552B2

(12) United States Patent
Zhou et al.

(10) Patent No.: US 10,376,552 B2
(45) Date of Patent: Aug. 13, 2019

(54) MEMORY IMPROVING COMPOSITION COMPRISING ARILLUS LONGAN, SEMEN NELUMBINIS, PORIA AND SEMEN JUGLANDIS

(71) Applicant: INFINITUS (CHINA) COMPANY LTD., Jiang Men (CN)

(72) Inventors: Yong Zhou, Jiang Men (CN); Xiaolei Guo, Jiang Men (CN); Chung Wah Ma, Jiang Men (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 301 days.

(21) Appl. No.: 15/252,528

(22) Filed: Aug. 31, 2016

(65) Prior Publication Data

US 2017/0071996 A1  Mar. 16, 2017

(30) Foreign Application Priority Data

Sep. 10, 2015  (CN) .......................... 2015 1 0573446

(51) Int. Cl.
```
A61K 36/52    (2006.01)
A61K 31/185   (2006.01)
A61K 31/685   (2006.01)
A61K 36/076   (2006.01)
A61K 36/185   (2006.01)
A61K 36/62    (2006.01)
A23L 33/105   (2016.01)
A61K 36/77    (2006.01)
A61K 38/01    (2006.01)
```
(52) U.S. Cl.
CPC ............ *A61K 36/52* (2013.01); *A23L 33/105* (2016.08); *A61K 31/185* (2013.01); *A61K 31/685* (2013.01); *A61K 36/076* (2013.01); *A61K 36/185* (2013.01); *A61K 36/62* (2013.01); *A61K 36/77* (2013.01); *A61K 38/011* (2013.01); *A23V 2002/00* (2013.01); *A61K 2236/15* (2013.01); *A61K 2236/19* (2013.01); *A61K 2236/331* (2013.01); *A61K 2236/53* (2013.01)

(58) Field of Classification Search
None
See application file for complete search history.

(56) References Cited

U.S. PATENT DOCUMENTS

| | | | | |
|---|---|---|---|---|
| 5,738,887 A | * | 4/1998 | Wu | .......................... A23F 3/10 |
| | | | | 426/51 |
| 2015/0258161 A1 | * | 9/2015 | Popp | ...................... A61K 36/11 |
| | | | | 424/479 |
| 2016/0113987 A1 | * | 4/2016 | Choi | .................... A61K 9/2018 |
| | | | | 424/439 |

FOREIGN PATENT DOCUMENTS

| | | | |
|---|---|---|---|
| CN | 1135294 | A | 11/1996 |
| CN | 1145198 | A | 3/1997 |
| CN | 103431374 | * | 12/2013 |
| CN | 104187613 | * | 12/2014 |
| DE | 102005003865 | A1 | 5/2007 |

OTHER PUBLICATIONS

Akito Kato-Kataoka et al., "Soybean-Derived Phosphatidylserine Improves Memory Function of the Elderly Japanese Subjects with Memory Complaints," *Journal of Clinical Biochemistry and Nutrition*, 47(3):246-255, Nov. 1, 2010.

Anonymous, "Juglans Regia (Walnut, Hu Tao)," retrieved from the Internet on Oct. 24, 2016: http://web.archive.org/web/20150501185850/ http://www.chineseherbshealing.com/juglans-regia-walnut/. May 1, 2015.

Anonymous, "Longan Fruit (Long Yan Rou)," retrieved from the Internet on Oct. 24, 2016: http://web.archive.org/web/20150501201050/ http://www.chineseherbshealing.com/longan-fruit/. May 1, 2015.

Anonymous, "Lotus Seed (Lotus Nut, Lian Zi)," retrieved from the Internet on Oct. 24, 2016: http://web.archive.org/web/20150516102025/ http://www.chineseherbshealing.com/lotus-seed/. May 16, 2015.

Anonymous, "Poria (Fu Ling)," retrieved from the Internet on Oct. 24, 2016: http://web.archive.org/web/20150501193654/http://www. chineseherbshealing.com/poria-fu-ling/. May 1, 2015.

(Continued)

*Primary Examiner* — Ralph J Gitomer
(74) *Attorney, Agent, or Firm* — Parker Highlander PLLC

(57) ABSTRACT

The present invention relates to the technical field of health food, and discloses a memory improving composition and the preparation method and use thereof. The composition is made from Arillus Longan, Poria, Semen Nelumbinis, enzymatic extract of Semen Juglandis, phosphatidylserine and taurine. In the present invention, the sovereign drug Arillus Longan is combined with ministerial drugs Poria and Semen Nelumbinis to synergistically achieve the effect of nourishing heart for tranquillization and tonifying kidney & invigorating spleen. They are further combined with enzymatic extract of Semen Juglandis improving brain metabolism and enhances memory, functional factor phosphatidylserine increasing fluidity and enhances plasticity of cell membrane, and taurine improving memory, to achieve the purpose of memory improvement together. All kinds of raw materials are medicine homologous and new resource food, which are safe, have no toxic and side effects, and thus can be consumed as health food over a long period of time.

5 Claims, No Drawings

(56) References Cited

OTHER PUBLICATIONS

Anonymous, "Traditional Chinese Medicine/Usage of Single Herbs Pulse," *Wikibooks*, retrieved from the Internet on Oct. 21, 2016: https://en.wikibooks.org/w/index.php?title=Traditional_Chinese_Medicine/Usage_Of SingleHerbs&oldid=2948354, pp. 1-48, Apr. 22, 2015.

Balu Muthaiyah et al., "Dietary supplementation of walnuts improves memory deficits and learning skills in transgenic mouse model of Alzheimer's disease," Journal of Alzheimer's Disease, 42(4):1397-1405, Oct. 1, 2014.

Bhupinder P. S. Vohra et al., "Improvement of Impaired Memory in Mice by Taurine," *Neural Plasticity*, 7(4):245-259, Jan. 1, 2000.

Extended European Search Report issued in European patent application No. 16186571.2, dated Nov. 9, 2016.

Hye Yun Kim et al., "Taurine in drinking water recovers learning and memory in the adult APP/PSI mouse model of Alzheimer's disease," *Scientific Reports*, 4:7467, Dec. 12, 2014.

\* cited by examiner

MEMORY IMPROVING COMPOSITION COMPRISING ARILLUS LONGAN, SEMEN NELUMBINIS, PORIA AND SEMEN JUGLANDIS

CROSS REFERENCE OF RELATED APPLICATION

This application claims the benefit of priority to Chinese Patent Application No. 201510573446.8 filed on Sep. 10, 2015. The entire content of the above-referenced disclosure is specifically incorporated herein by reference.

FIELD

The present invention relates to the technical field of health food, and particularly to a memory improving composition and the preparation method and use thereof.

BACKGROUND

With the quick pace of life, the increasing pressure of living, the incidence of symptoms such as forgetfulness and insomnia is increasing. There is a trend for such symptoms to affect younger people. Forgetfulness can be caused by many factors, in addition to age, excessive use of the brain, excessive stress, lack of sleep, bad mood, bad habits, and so on will lead to decline of memory. Forgetfulness is an important symptom of decreased brain function. In traditional Chinese medicine, it is believed that memory decline is a comprehensive and complex disorder involving multiple visceral organs. The nidus mainly locates in heart, spleen, and kidney, which ultimately results in disturbance of mind by pathogen or lack of mind nourishment through evolution in multiple visceral organs, with the internal pathological basis being deficiency of heart, spleen and kidney. Memory decline seriously affects normal work and study, and leads to much inconvenience and trouble in normal life. Therefore, how to improve memory becomes one of hot topics in society.

At present, people usually consume traditional food, crude medicine, etc. which are beneficial to the brain and intelligence over a long period of time to achieve the effect of memory improvement. However, the effect of diet therapy for improving memory is not outstanding. In addition, nootropic drugs such as Huperzine A, which are clinically used as cholinesterase inhibitors for treatment of benign memory disorder and senile dementia, have side-effects of nausea, dizziness, sweating, abdominal pain, and blurred vision after ingestion. Thus, they are not suitable for regular use over a long period of time. Therefore, it will become an urgent need to develop health food which can be consumed over a long period of time with significant effects, safety, and no toxic & side effects.

SUMMARY

In view of the above need, it is an object of the present invention to provide a memory improving composition, which can be consumed as health food over a long period of time with memory improving effect, safety, and no side effects. Meanwhile, a preparation method of the composition and its use in memory improving health food are also provided.

In order to achieve the above objects, the present invention provides the following technical solutions.

A memory improving composition, which is made from Arillus Longan, Poria, Semen Nelumbinis, enzymatic extract of Semen Juglandis, phosphatidylserine and taurine, the enzymatic extract of Semen Juglandis being a hydrolysate of Semen Juglandis dregs after hydrolyzation with alkaline endoprotease Alcalase 2.4 L and complex protease Protamex. Walnut protein is the one common in the art obtained by the method of alkali extraction and acid precipitation using Semen Juglandis or Semen Juglandis dregs as raw material. Furthermore, the hydrolysate comprises free amino acids, dipeptide, tripeptide and polypeptide substances produced by further hydrolyzation of walnut protein by the above two kinds of proteases.

According to the compound prescription theory in traditional Chinese medicine, in the present invention, the sovereign drug Arillus Longan is combined with Poria and Semen Nelumbinis with effects of anti-aging, anti-oxidation and the like. They are further combined with enzymatic extract of Semen Juglandis which improves brain metabolism and enhances memory, functional factor phosphatidylserine which increases fluidity and enhances plasticity of cell membrane, and taurine which improves memory, for overall conditioning in order to perform the best health efficacy and improve memory together. Meanwhile, raw materials in the composition of the present invention are medicine homologous and new resource food, which are safe, have no toxic and side effects, and thus can be consumed as health food over a long period of time.

Preferably, the composition is prepared by extracting Arillus Longan, Poria and Semen Nelumbinis by water decoction, and mixing with enzymatic extract of Semen Juglandis, phosphatidylserine and taurine.

Preferably, parts by weight of the respective raw materials are:

200~800 parts of Arillus Longan, 200~800 parts of Semen Nelumbinis, 200~800 parts of Poria, 10~150 parts of enzymatic extract of Semen Juglandis, 10~150 parts of phosphatidylserine, and 3~50 parts of taurine.

In some specific embodiments of the present invention, respective raw materials can also be selected as follows:

200 parts of Arillus Longan, 800 parts of Semen Nelumbinis, 200 parts of Poria, 150 parts of enzymatic extract of Semen Juglandis, 10 parts of phosphatidylserine, and 50 parts of taurine;

800 parts of Arillus Longan, 200 parts of Semen Nelumbinis, 800 parts of Poria, 10 parts of enzymatic extract of Semen Juglandis, 150 parts of phosphatidylserine, 3 parts of taurine;

600 parts of Arillus Longan, 500 parts of Semen Nelumbinis, 600 parts of Poria, 80 parts of enzymatic extract of Semen Juglandis, 100 parts of phosphatidylserine, and 40 parts of taurine; or 400 parts of Arillus Longan, 600 parts of Semen Nelumbinis, 500 parts of Poria, 50 parts of enzymatic extract of Semen Juglandis, 30 parts of phosphatidylserine, and 10 parts of taurine.

The enzymatic extract of Semen Juglandis in the present invention comprises polypeptides produced by hydrolyzation of walnut protein with alkaline endoprotease Alcalase 2.4 L and complex protease Protamex. As a further preferred procedure, it is prepared by the following process:

step 1: grinding Semen Juglandis dregs in water to obtain a slurry of Semen Juglandis dregs, adding alkali to adjust the pH value to 8.0 to 9.0, centrifuging, removing impurities in the supernatant enzymatically, adding acid to cause precipitation, washing the precipitate to obtain the walnut protein;

step 2: hydrolyzing the walnut protein to a hydrolysis degree of 8-12% with alkaline endoprotease Alcalase 2.4 L and complex protease Protamex, and collecting the supernatant as enzymatic hydrolysate of walnut protein after enzyme deactivation and centrifugation;

step 3: enriching enzymatic extract of Semen Juglandis by separating the enzymatic hydrolysate of walnut protein through a filter cloth and ultrafiltration membrane.

Preferably, removing impurities in the supernatant enzymatically in step 1 is carried out by adding 1% of α-amylase and 0.5% of cellulase relative to the total weight of the Semen Juglandis dregs to the supernatant.

Preferably, in step 1, the alkali used is sodium hydroxide, and adding acid to cause precipitation is carried out by adding 1 mol/L HCl solution to adjust pH to 4.2, stirring for 30-60 minutes, and centrifuging to obtain the precipitate.

Preferably, step 1 is carried out as follows:

adding 10 to 15 parts by weight of water to 1 part of Semen Juglandis dregs, obtaining the slurry of Semen Juglandis dregs after passing through a colloid mill, adjusting pH of the slurry to 8.0-9.0 by adding NaOH solution (1 mol/L), stirring for 60-90 min at 40-50° C., then centrifuging for 10 min at 3500 r/min, and filtering to obtain the supernatant; adding hydrolase to the supernatant for enzymatically removing impurities therein, then adding HCl solution (1 mol/L) to adjust pH to 4.2, stirring for 30-60 min, centrifuging to obtain the precipitate, stirring with addition of a certain concentration of ethanol, washing with water, and performing spray drying to obtain the walnut protein.

Preferably, step 2 is carried out as follows:

stirring the walnut protein with addition of water, adding alkaline endoprotease Alcalase 2.4 L in an amount of 2000-3000 U/g protein and complex protease Protamex in an amount of 1200-2500 U/g protein, hydrolyzing to a hydrolysis degree of 8-12% at 50-55° C., and collecting the supernatant after enzyme deactivation and centrifugation to obtain the enzymatic hydrolysate of walnut protein.

Preferably, step 3 is carried out as follows:

filtering the enzymatic hydrolysate of walnut protein through a 100 mesh filter cloth, then through an ultrafiltration membrane with a membrane flux of 10000 Da, collecting the permeation liquid, then filtering it through an ultrafiltration membrane with a membrane flux of 1000 Da, collecting the retentate to obtain a walnut polypeptide solution, which is concentrated under vacuum to achieve a solid content of 30-40% and spray dried to obtain the enzymatic extract of Semen Juglandis.

Meanwhile, the present invention also provides a method of preparing the composition, which comprises extracting Arillus Longan, Poria and Semen Nelumbinis by water decoction, performing concentration and spray drying of the extract, adding taurine, phosphatidylcholine and the enzymatic extract of Semen Juglandis and mixing evenly to obtain the composition.

The efficacy of the composition of the present invention was tested in accordance with the "health food inspection and evaluation standard". Latency of swimming and swimming distance in a mice Morris water maze recognition experiment as well as latency and error times in a mice step-down test were used as observed indexes to evaluate the effect of the composition of the present invention on memory improvement in experimental animals. The results show that the composition of the present invention has an improving and intelligence-promoting effect on memory disorder. Meanwhile, during long-term toxicity tests in rats, the rats were continuously fed with the composition of the present invention for 90 days, and there was no significant difference in body weight, hematological indexes, blood biochemical indexes and tissue pathological state, etc., compared with the normal group, which proves that the composition of the present invention is highly safe and can be consumed over a long period of time.

Based on the above advantageous effects, the present invention provides use of the composition in the preparation of memory improving health food. The present invention also provides a method of preparing a memory improving health food, wherein the health food comprises the composition of the present invention. Preferably, the health food is in the form of tablets, capsules, powders, granules, effervescent preparations, beverages, misturas or oral liquids.

After obtaining the composition of the present invention, those skilled in the art are able to prepare the composition into an appropriate dosage form according to manufacture requirements of conventional dosage forms and the general choice of excipients. These dosage forms include, but are not limited to tablets, capsules, powders, granules, effervescent preparations, beverages, misturas or oral liquids. The excipients can be selected from such as microcrystalline cellulose, pre-gelatinized starch, magnesium stearate, cross-linked sodium carboxymethyl cellulose, lactose, corn starch, wheat starch, rice starch, potato starch, polyvinylpyrrolidone, calcium phosphate, methyl silicone oil, sucrose, mannitol, sorbitol, gelatin, tragacanth and the like.

As can be seen from the above technical solutions, in the present invention, the sovereign drug Arillus Longan is combined with ministerial drugs Poria and Semen Nelumbinis to synergistically achieve the effect of nourishing heart for tranquillization and tonifying kidney & invigorating spleen. They are further combined with enzymatic extract of Semen Juglandis which improves brain metabolism and enhances memory, functional factor phosphatidylserine which increases fluidity and enhances plasticity of cell membrane, and taurine which improves memory, to achieve the purpose of memory improvement together. All kinds of raw materials are medicine homologous and new resource food, which are safe, have no toxic and side effects, and thus can be consumed as health food over a long period of time.

DETAILED DESCRIPTION

The present invention discloses a memory improving composition, the preparation method and use thereof, which can be carried out by those skilled in the art by appropriately improving process parameters in light of the contents herein. In particular, it is to be noted that all similar substitutions and alterations are obvious to the skilled in the art, and are deemed to be included in the present invention. The composition of the present invention and the preparation method and use thereof have been described through preferred examples, and it is obvious for related personnel to make alterations and appropriate modifications or combinations to the method and use described herein without departing from the content, spirit and scope of the present invention in order to realize and apply the invention.

The memory improving composition and the preparation method and use thereof provided in the present invention will be further illustrated as follows.

Example 1: Composition of the Present Invention

1. Raw Materials 400 parts of Arillus Longan, 600 parts of Semen Nelumbinis, 500 parts of Poria, 50 parts of enzymatic extract of Semen Juglandis, 30 parts of phosphatidylserine, and 10 parts of taurine.

2. Preparation Method (1) Preparation of enzymatic extract of Semen Juglandis 10 to 15 parts by weight of water was added to 1 part of Semen Juglandis dregs. A slurry of Semen Juglandis dregs was obtained after passing the mixture through a colloid mill. The pH of the slurry was adjusted to 8.0-9.0 by addition of NaOH solution (1 mol/L). The slurry was stirred for 60-90 min at 40-50° C., then centrifuged for 10 min at 3500 r/min, and filtered to obtain a supernatant. A-amylase in an amount of 1% of the total weight of Semen Juglandis dregs and cellulase in an amount of 0.5% of the total weight of Semen Juglandis dregs were added to the supernatant for enzymatically removing impurities, followed by addition of HCl solution (1 mol/L) to adjust pH to 4.2, agitation for 30-60 min, and centrifugation to obtain a precipitate. The precipitate was stirred with addition of a certain concentration of ethanol, washed with water, and subjected to spray drying to obtain the walnut protein.

The walnut protein was stirred with addition of water, added with alkaline endoprotease Alcalase 2.4 L (purchased from Novozymes) in an amount of 2000-3000 U/g protein and complex protease Protamex (purchased from Novozymes) in an amount of 1200-2500 U/g protein, and hydrolyzed to a hydrolysis degree of 8-12% at 50-55° C. The enzyme was deactivated. After centrifugation, the supernatant was collected as the enzymatic hydrolysate of walnut protein.

The enzymatic hydrolysate of walnut protein was filtered through a 100 mesh filter cloth, then through an ultrafiltration membrane with a membrane flux of 10000 Da. The permeation liquid was collected, then filtered through an ultrafiltration membrane with a membrane flux of 1000 Da. The retentate was collected to obtain a walnut polypeptide solution, which was concentrated under vacuum to achieve a solid content of 30-40% and spray dried to obtain the enzymatic extract of Semen Juglandis.

(2) The raw material drugs Arillus Longan, Poria and Semen Nelumbinis were extracted by water decoction. The resultant extract was concentrated and subjected to spray drying. Taurine, phosphatidylserine and the enzymatic extract of Semen Juglandis were added and mixed well to obtain the composition.

Example 2: Traditional Chinese Medicine Composition of the Present Invention

1. Raw Materials 600 parts of Arillus Longan, 500 parts of Semen Nelumbinis, 600 parts of Poria, 80 parts of enzymatic extract of Semen Juglandis, 100 parts of phosphatidylserine, and 40 parts of taurine.

2. Preparation Method

The same as the example 1.

Example 3: Traditional Chinese Medicine Composition of the Present Invention

1. Raw Materials 200 parts of Arillus Longan, 800 parts of Semen Nelumbinis, 200 parts of Poria, 150 parts of enzymatic extract of Semen Juglandis, 10 parts of phosphatidylserine, and 50 parts of taurine.

2. Preparation Method

The same as the example 1.

Example 4: Traditional Chinese Medicine Composition of the Present Invention

1. Raw Materials 800 parts of Arillus Longan, 200 parts of Semen Nelumbinis, 800 parts of Poria, 10 parts of enzymatic extract of Semen Juglandis, 150 parts of phosphatidylserine, and 3 parts of taurine.

2. Preparation Method

The same as the example 1.

Example 5: Experimental Study of the Long-Term Toxicity of the Composition of the Present Invention in Rats 1. Test sample: composition of the example 1.

2. Test animals: 140 wistar rats, SPF grade, body weight 100-150 g, with half male and half female, provided by the Experimental Animal Center of Zhongshan University, Guangzhou;

3. Experimental design was carried out according to "food safety toxicology evaluation procedures" of "implementation manual of health food inspection and evaluation technical specification" (2003 edition).

4. Dose design and grouping. A blank control group and low, medium and high dosage groups of AS1322-02 health food were set. The animals that had undergone quarantine were weighed. Each group contained 20 rats, with half male and half female. The specific dosages 1.33 g·kg$^{-1}$, 4.0 g·kg$^{-1}$ and 8.0 g·kg$^{-1}$ correspond to 10 times, 30 times and 60 times of the recommended dosage for human.

5. Method of administration. The test sample was dissolved in distilled water and diluted to the specified concentration, and was intragastrically administered. The rats were intragastrically administered at the same time period once a day. The administration volume was 2 ml per 100 g body weight. The body weight was weighed once a week during the experiment, and the administration volume was adjusted according to the weight. The rats were continuously administered for 90 days. The animals in each group were fasted for 15 h after the last administration, and samples were taken on the next day.

6. Effect of the composition on the general condition and body weight of rats. The mental state of female and male animals in each group was good. They had smooth and bright coat colors, moved about freely, breathed evenly. There was no significant abnormality in their food intake and stool. There was no abnormal secretion in their nose and mouth. Compared with the blank control group, there was no significant difference in body weights of animals in respective test sample groups (each P>0.05), and weight gain was even. Details are shown in Table 1.

TABLE 1

Effect of the composition on the body weight of rats ( g, n = 20, $\bar{\chi} \pm s$)

| Time/weeks | Blank control group ♀ | Blank control group ♂ | Low dosage group ♀ | Low dosage group ♂ | Medium dosage group ♀ | Medium dosage group ♂ | High dosage group ♀ | High dosage group ♂ |
|---|---|---|---|---|---|---|---|---|
| 0  | 81 ± 10  | 113 ± 8  | 84 ± 10  | 114 ± 14 | 82 ± 9   | 119 ± 11 | 83 ± 7   | 112 ± 10 |
| 1  | 131 ± 17 | 165 ± 11 | 142 ± 17 | 162 ± 18 | 126 ± 11 | 172 ± 16 | 130 ± 16 | 164 ± 10 |
| 2  | 162 ± 17 | 213 ± 16 | 172 ± 15 | 203 ± 19 | 155 ± 15 | 214 ± 22 | 164 ± 16 | 211 ± 13 |
| 3  | 187 ± 15 | 248 ± 16 | 191 ± 14 | 239 ± 19 | 180 ± 16 | 253 ± 30 | 190 ± 14 | 247 ± 12 |
| 4  | 203 ± 15 | 278 ± 12 | 206 ± 13 | 268 ± 20 | 198 ± 15 | 275 ± 20 | 211 ± 12 | 278 ± 15 |
| 5  | 213 ± 17 | 306 ± 16 | 219 ± 12 | 294 ± 22 | 214 ± 13 | 302 ± 23 | 222 ± 11 | 306 ± 17 |
| 6  | 223 ± 17 | 326 ± 14 | 228 ± 12 | 316 ± 20 | 225 ± 10 | 321 ± 20 | 228 ± 11 | 327 ± 16 |
| 7  | 233 ± 18 | 343 ± 13 | 238 ± 13 | 336 ± 19 | 234 ± 10 | 341 ± 17 | 234 ± 15 | 342 ± 13 |
| 8  | 240 ± 17 | 359 ± 13 | 247 ± 12 | 351 ± 20 | 243 ± 10 | 359 ± 16 | 240 ± 13 | 357 ± 11 |
| 9  | 246 ± 16 | 372 ± 12 | 253 ± 13 | 365 ± 25 | 249 ± 9  | 372 ± 14 | 248 ± 16 | 369 ± 9  |
| 10 | 253 ± 17 | 382 ± 13 | 260 ± 12 | 383 ± 20 | 257 ± 10 | 388 ± 13 | 252 ± 15 | 382 ± 12 |
| 11 | 258 ± 15 | 392 ± 12 | 266 ± 13 | 392 ± 19 | 262 ± 9  | 397 ± 12 | 261 ± 17 | 393 ± 13 |
| 12 | 263 ± 15 | 401 ± 11 | 271 ± 13 | 403 ± 17 | 269 ± 9  | 407 ± 12 | 266 ± 17 | 402 ± 12 |
| 13 | 268 ± 16 | 411 ± 12 | 277 ± 13 | 412 ± 17 | 274 ± 9  | 416 ± 11 | 269 ± 18 | 413 ± 12 |

Note:
There was no significant difference among the groups.

7. Effect of the composition on visceral coefficient of rats.

As shown in Table 2, compared with the blank control group, the heart, liver, spleen, lung, brain and kidney coefficients of rats in respective dosage groups of the test sample showed no significant difference (each P>0.05).

TABLE 2

Effect of the composition on visceral coefficient of rats (n = 20, $\bar{\chi} \pm s$)

| Groups | Heart | Liver | Spleen | Lung | Brain | Kidney |
|---|---|---|---|---|---|---|
| Blank control group | 3.03 ± 0.33 | 32.56 ± 4.32 | 2.54 ± 0.39 | 5.42 ± 0.81 | 3.32 ± 0.18 | 6.65 ± 0.70 |
| Low dosage group | 2.90 ± 0.08 | 28.18 ± 3.79 | 2.33 ± 0.22 | 5.81 ± 0.85 | 3.57 ± 0.41 | 6.56 ± 0.58 |
| Medium dosage group | 3.16 ± 0.21 | 31.47 ± 4.97 | 3.16 ± 0.79 | 5.47 ± 0.53 | 3.49 ± 0.43 | 6.21 ± 0.44 |
| High dosage group | 3.18 ± 0.19 | 35.15 ± 2.28 | 2.44 ± 0.36 | 5.22 ± 0.46 | 3.36 ± 0.39 | 6.71 ± 0.90 |

Note:
There was no significant difference among the groups.

8. Effect of the composition on blood routine of rats.

As shown in Table 3, compared with the blank control group, the red blood cell count (RBC), hemoglobin content (HGB), platelet count (PLT), (BA), white blood cell count (WBC), lymphocyte relative count (LY), monocyte relative count (MO), neutrophil relative count (NE), and eosinophils (EO) in respective dosage groups of the test sample showed no significant difference (each P>0.05).

TABLE 3

Effect of the composition on blood routine of rats

| Groups | RBC ($10^{12}$/L) | HGB (g/L) | PLT ($10^9$/L) | BA (%) | WBC ($10^9$/L) |
|---|---|---|---|---|---|
| Blank control group | 7.81 ± 0.57 | 147.86 ± 13.18 | 961.43 ± 101.43 | 0.19 ± 0.04 | 11.66 ± 0.38 |
| Low dosage group | 8.20 ± 0.25 | 160.94 ± 12.72 | 969.71 ± 101.35 | 0.14 ± 0.05 | 12.75 ± 1.57 |
| Medium dosage group | 8.19 ± 0.32 | 158.46 ± 8.65 | 869.86 ± 237.32 | 0.14 ± 0.05 | 13.39 ± 2.17 |
| High dosage group | 8.20 ± 0.21 | 156.40 ± 12.42 | 844.14 ± 227.72 | 0.23 ± 0.08 | 11.25 ± 1.62 |

| Groups | LY (%) | MO (%) | NE (%) | EO (%) |
|---|---|---|---|---|
| Blank control group | 69.47 ± 4.97 | 3.26 ± 1.08 | 24.96 ± 5.08 | 2.13 ± 1.26 |
| Low dosage group | 70.59 ± 9.25 | 2.33 ± 0.53 | 22.73 ± 9.54 | 3.79 ± 2.03 |
| Medium dose group | 73.64 ± 3.41 | 2.34 ± 0.86 | 20.60 ± 4.90 | 3.57 ± 2.42 |
| High dosage group | 73.10 ± 3.16 | 2.11 ± 0.93 | 22.80 ± 3.23 | 1.63 ± 1.30 |

Note:
There was no significant difference among the groups.

9. Effect of the composition on blood biochemistry of rats.

As shown in the table 4, compared with the blank control group, the alkaline phosphatase (ALP), blood glucose (GLU), urea nitrogen (BUN), creatinine (CREA), alanine aminotransferase (ALT), aspartate aminotransferase (AST), total bilirubin (TBIL), total protein (TP), albumin (ALB), and total cholesterol (CHOL) in respective dosage groups of the test sample showed no significant difference (each $P>0.05$).

TABLE 4

Effect of the composition on blood biochemistry of rats

| Groups | ALP | GLU | BUN | CREA | ALT |
|---|---|---|---|---|---|
| Blank control group | 140.23 ± 12.01 | 4.09 ± 0.76 | 8.29 ± 0.91 | 140.72 ± 32.63 | 85.77 ± 14.25 |
| Low dosage group | 121.56 ± 19.81 | 4.71 ± 0.72 | 8.03 ± 1.04 | 133.12 ± 12.82 | 74.10 ± 5.79 |
| Medium dosage group | 128.50 ± 42.52 | 4.62 ± 0.64 | 7.74 ± 0.89 | 132.29 ± 13.75 | 69.66 ± 23.27 |
| High dosage group | 115.81 ± 41.41 | 4.90 ± 0.79 | 7.59 ± 0.74 | 166.38 ± 45.48 | 68.82 ± 25.14 |

| Groups | AST | TBIL | TP | ALB | CHOL |
|---|---|---|---|---|---|
| Blank control group | 126.53 ± 39.38 | 43.87 ± 12.70 | 80.06 ± 3.26 | 44.65 ± 3.02 | 1.66 ± 0.23 |
| Low dosage group | 137.67 ± 36.34 | 41.21 ± 9.93 | 81.94 ± 4.70 | 42.52 ± 1.21 | 1.48 ± 0.26 |
| Medium dosage group | 118.13 ± 44.55 | 50.81 ± 11.35 | 82.81 ± 2.46 | 42.62 ± 3.29 | 1.49 ± 0.09 |
| High dosage group | 114.29 ± 20.16 | 38.44 ± 18.97 | 79.52 ± 6.66 | 43.08 ± 3.42 | 1.63 ± 0.49 |

Note:
There was no significant difference among the groups.

Based on the above results, the long-term administration of the composition of the present invention within the condition and dosage range of the experiments did not affect the general state and body weight of the test rats, and no significant toxicity was caused to the main visceral organs and blood system, i.e., no toxicity reaction was caused, which suggests the higher safety of the composition for consuming at the recommended dose for a long time.

Example 6: Animal Experiments on the Protective Effect of the Composition of the Present Invention on Memory Disorder 1. Animal Grouping Mice were randomly divided into 5 groups evenly, namely, normal control group, model group, low dosage group, high dosage group, positive control drug Huperzine A group (0.1 mg/kg). The mice were intragastrically administered once daily (0.2 mL/10 g). After 30 consecutive days, except the normal control group, the memory acquired disorder model of mice was replicated respectively with scopolamine, and the learning performance of mice was determined with the Morris water maze test (scopolamine-induced orientation navigation and spatial memory experiment).

2. Preparation of Test Samples

In accordance with technical requirements including "technical specifications of health food inspection and evaluation", the dosage was calculated by conversion of the intended clinical daily dosage on the basis of the body surface area. When orally administered to mice, low and high dosages were arranged for each sample, respectively, which correspond to about 10 and 20 times of intended daily dosage for adults. Namely: low dosage group (1.3 g/kg), high dosage group (2.6 g/kg).

As for the positive control drug Huperzine A, the clinical adult dosage is about 0.4 mg/day, and the dosage for mice is 0.06 mg/kg, which is calculated by conversion on the basis of the body surface area. 0.1 mg/kg was used in the present experiment.

The mice were intragastrically administered once daily (0.2 mL/10 g). After 30 consecutive days, except the normal control group, the memory acquired disorder model of mice was replicated respectively with scopolamine, and the learning performance of mice was determined with the Morris water maze test (scopolamine-induced orientation navigation and spatial memory experiment).

3. Detection Indexes

Morris water maze test was carried out according to the method in references. The orientation navigation test was started from the $25^{th}$ day, and lasted for 4 consecutive days. The time of finding the platform of mice within 90 s (the escape latency), swimming distance, the swimming time proportion in the quadrant of the original platform, times of crossing the location of the original platform (i.e., shuttle times), and the time of first arrival at the original platform were recorded.

4. Experimental Method

Research Experiment of the Protective Effect on Memory Disorder—Water Maze Test

Mice were randomly divided into 5 groups, namely, normal control group, model group, low dosage group (1.3 g/kg), high dosage group (2.6 g/kg), positive control drug Huperzine A group (0.1 mg/kg). The mice were intragastrically administered once daily (0.2 mL/10 g). After 30 consecutive days, except the normal control group, the memory acquired disorder model of mice was replicated respectively with scopolamine, and the learning performance of mice was determined with the Morris water maze test (scopolamine-induced orientation navigation and spatial memory experiment).

5. Statistic Analysis

All experimental data were expressed as $\bar{x}\pm s$. The homogeneity test of variance was firstly carried out with variance analysis. F value was calculated. If F value was $<F_{0.05}$, it could be concluded that there was no significant difference among mean values of various groups. If F value≥$F_{0.05}$ and P≤0.05, statistic analysis was carried out by using the method of pairwise comparison of mean values among a plurality of experimental groups and a control group. Appropriate variable conversion was carried out for data with non-normality or heterogeneity of variance, and the converted data were used for statistic analysis after the requirement of normality or homogeneity of variance was satisfied. If the purpose of normality or homogeneity of variance was still not achieved after conversion, rank sum test was employed instead for statistic analysis.

6. Determination of Results

In accordance with "technical specifications of health food inspection and evaluation" (2003 edition), the effect of the test samples on improving memory disorder was determined according to the following criteria.

The experimental results of the protective effect of the composition of the present invention on memory disorder have statistic significance, and the results were shown in Tables 5-7.

TABLE 5

Effect on swimming latency (s) of mice in water maze (orientation navigation test) ($\overline{X} \pm s$, n = 12).

| Groups | Day 1 | Day 2 | Day 3 | Day 4 |
| --- | --- | --- | --- | --- |
| Normal control group | 67.2 ± 16.3 | 60.3 ± 12.3 | 52.1 ± 10.3 | 36.5 ± 6.8 |
| Model group | 68.4 ± 14.5 | 64.2 ± 10.2 | 60.2 ± 9.8$^\Delta$ | 55.6 ± 11.3$^{\Delta\Delta}$ |
| Low dosage group | 67.2 ± 15.5 | 61.9 ± 8.6 | 55.0 ± 8.5 | 49.1 ± 6.5 |
| High dosage group | 67.3 ± 17.2 | 62.0 ± 11.6 | 56.1 ± 9.9 | 47.2 ± 7.2 |
| Huperzine A | 68.3 ± 15.6 | 59.1 ± 13.8 | 56.3 ± 13.1 | 48.8 ± 11.1 |

Note:
Compared with the normal control group, $^\Delta p < 0.05$, $^{\Delta\Delta} p < 0.01$;
compared with the model group, *p < 0.05, **p < 0.01.

TABLE 6

Effect on swimming distance (cm) of mice in water maze (orientation navigation test) ($\overline{X} \pm s$, n = 12)

| Groups | Day 1 | Day 2 | Day 3 | Day 4 |
| --- | --- | --- | --- | --- |
| Normal control group | 864.5 ± 131.1 | 743.7 ± 159.7 | 586.0 ± 130.1 | 493.0 ± 146.0 |
| Model group | 890.6 ± 126.6 | 774.6 ± 125.0 | 740. ± 128.8$^{\Delta\Delta}$ | 702.2 ± 139.7$^{\Delta\Delta}$ |
| AS1322-02 low | 870.3 ± 170.1 | 778.9 ± 151.9 | 736.8 ± 93.9 | 677.2 ± 97.8 |
| AS1322-02 high | 882.3 ± 133.5 | 755.3 ± 179.3 | 720.6 ± 121.5 | 675.6 ± 108.9 |
| Huperzine A | 892.9 ± 226.6 | 747.2 ± 93.5 | 683.3 ± 112.8 | 669.6 ± 128.3 |

Note:
Compared with the normal control group, $^\Delta p < 0.05$, $^{\Delta\Delta} p < 0.01$;
compared with the model group, *p < 0.05, **p < 0.01.

As can be seen from Tables 5 and 6, with the increase of training time, the swimming latency and distance of mice in respective groups were gradually reduced during a four-day cognitive training, indicating that the memory disorder model of mice was successfully established. Compared with the model group, the latency of mice in each dosage group of the samples was shortened, but there was no statistic difference.

TABLE 7

Effect on scopolamine hydrobromide-induced mice memory acquired disorder model (space exploration test) ($\overline{X} \pm s$, n = 12).

| Groups | Time of first arrival at the platform (s) | Time proportion of crossing the original quadrant (%) | Shuttle times |
| --- | --- | --- | --- |
| Normal control group | 25.5 ± 11.4 | 25.1 ± 6.9 | 2.8 ± 0.9 |
| Model control group | 46.9 ± 21.1$^{\Delta\Delta}$ | 16.5 ± 8.4$^\Delta$ | 1.4 ± 0.7$^{\Delta\Delta}$ |
| Low dosage group | 30.5 ± 10.9* | 20.1 ± 7.6 | 1.9 ± 0.6 |
| High dosage group | 28.5 ± 11.3* | 22.1 ± 7.6 | 2.0 ± 0.6 |
| Huperzine A | 27.0 ± 12.1* | 22.6 ± 7.9 | 2.2 ± 0.5* |

Note:
Compared with the normal control group, $^\Delta p < 0.05$, $^{\Delta\Delta} p < 0.01$;
compared with the model group, * p < 0.05, **p < 0.01.

As can be seen from Table 7, compared with the normal control group, the swimming time at the quadrant of the original platform was significantly shortened in mice of the model control group (p<0.05), the time of first arrival at the platform was significantly prolonged (p<0.01), and the times of crossing the location of the original platform for mice was significantly decreased (p<0.01). Compared with the model control group, there is a trend of prolongation for the swimming time at the quadrant of the original platform of mice in the low and high dosage groups (p>0.05); the time of first arrival at the platform of mice in the low and high dosage groups was significantly shortened (p<0.05); the times of crossing the original platform of mice was significantly increased (p>0.05). The positive drug Huperzine A was capable of significantly prolonging the time of first arrival at the platform of mice (p<0.05), and the times of crossing the location of the original platform of mice was significantly decreased (p<0.05). This suggested that scopolamine damaged the spatial memory ability of mice, while the product can reverse the damage of scopolamine on the spatial memory of mice. It indicated that the test samples in this experiment improved the memory disorder in the mice of scopolamine model to some degree. The administered dosage and survival time after poisoning in the animals of the experimental groups had dosage-effect relationship, and the survival time of high dosage group was significantly increased.

In this example, respective groups of animals were adaptively fed for 3 days before intragastrical administration. The normal control group and model control group were intragastrically administered once daily with equal volume of 0.5% CMCNA, respectively. The administration was carried out with a volume of 0.2 mL/10 g body weight for 30 consecutive days. Morris water maze test was carried out according to the method in literatures. The orientation navigation test was started from the $25^{th}$ day, and lasted for 4 days. The time of finding the platform of mice within 90 s (the escape latency), swimming distance, the swimming time proportion in the quadrant of the original platform, times of crossing the location of the original platform (i.e., shuttle times), and the time of first arrival at the original platform were recorded. Various groups had a significant difference, showed an obvious dose-effect relationship, and the high dosage group had a significantly effect.

According to the "technical specifications of health food inspection and evaluation" (2003 edition), the conclusion of this animal experiment was that the test samples could improve memory.

Example 7: Animal Experiments of Protective Effect of the Composition of the Present Invention on Memory Acquisition The main symptom of memory decline is learning and memory disorder. The effect of a medicament on treatment of memory decline was often determined through intelligence indexes test by virtue of animal models of learning and memory disorder in modern research.

According to the "technical specifications of health food inspection and evaluation" (2003 edition), the learning performance of the experimental animals were measured through the memory acquired disorder model and step-down test. If there is a significant difference among the results of various groups, the effect of improving memory of the test sample is determined.

The indexes of various groups had significant difference in the step-down test of mice between the two dosage groups of the composition of the present invention, showed an obvious dose-effect relationship, and the high dosage group had a significant effect. The conclusion of this animal experiment was that the test samples could improve memory.

1. Animal Grouping

Mice were randomly divided into 5 groups, namely, normal control group, model group, low dosage group, high dosage group, positive control drug Huperzine A group (0.1 mg/kg). The mice were intragastrically administered once daily (0.2 mL/10 g). After 30 consecutive days, except the normal control group, the memory acquired disorder model of mice was replicated respectively with 5 mg/kg of scopolamine hydrobromide, and the learning performance of mice was determined with the step-down test.

2. Preparation of Test Samples

In accordance with technical requirements including "technical specifications of health food inspection and evaluation", the dosage was calculated by conversion of the intended clinical daily dosage on the basis of the body surface area. When orally administered to mice, low and high dosages were arranged for each sample, respectively, which correspond to about 10 and 20 times of intended daily dosage for adults. Namely: low dosage group (1.3 g/kg), high dosage group (2.6 g/kg).

As for the positive control drug Huperzine A, the clinical adult dosage is about 0.4 mg/day, and the dosage for mice is 0.06 mg/kg, which is calculated by conversion on the basis of the body surface area. 0.1 mg/kg was used in the present experiment.

3. Detection Indexes

The time of the first jumping of mice (i.e., latency) and the times of jumping of mice within 5 minutes (i.e., errors times) were tested and recorded with jumping apparatus, and the latency and error times were used as the investigation indexes of the experiment.

4. Experimental Method 60 screened healthy adult Kunming mice were used, with body weight (20-24) g, male, 12 rats in each group. Mice were randomly divided into 5 groups, namely, normal control group (C), model group (M), low dosage group (1.3 g/kg), high dosage (2.6 g/kg), positive control drug Huperzine A group (0.1 mg/kg). Except that the normal control group and model group were intragastrically administered with 0.5% CMCNA (0.2 mL/10 g), other groups were intragastrically administered with corresponding drugs once daily for 30 consecutive days. Training was started 1 h after administration in the morning on day 30. Except the normal control group, the memory acquired disorder model of mice was replicated respectively with 2 mg/kg scopolamine hydrobromide 20 minutes before training. Each group was administered in parallel, and the learning performance of mice was determined by step-down test.

The training method of mice in step-down test and observation indexes are as follows.

The device of mice step-down test was a square box which was 30 cm high with an electric fence (10 cm×10 cm) (voltage 36V) at the bottom. Inside the box was a platform with a height of 3.2 cm and diameter of 4.2 cm. The experiment was divided into the following phases:

(1) adaptive period: the animals were placed on the platform, at that time the electric fence was not energized, the latency of jumping down the platform was recorded, the animals were allowed to freely explore 10 s in the test box after jumping down the platform, and were then returned to the cage;

(2) training: the jumping apparatus was connected to the variable transformer firstly, and the voltage was controlled at 36V during training; 5-6 mice of the first batch were placed on the platform in corresponding grids in the jumping apparatus when training was started, the animals were given 36V electrical stimulation for 2-3 s immediately when they jumped down the platform, and then they were returned to the cage;

(3) testing: 24 h after learning experiments, the animals were put back on the platform, and the stopwatch was started at the same time; the time of the first jumping of mice (i.e., latency) and the times of jumping of mice within 5 minutes (i.e., errors times) were tested and recorded, the latency and error times were used as the investigation indexes of the experiment, and prolongation of the latency and/or reduction of errors times showed that learning and memory ability of animals were enhanced; if mice in the test did not jump down the round rubber platform within 5 minutes, the latency was recorded as 300 s.

The learning performance was tested after 24 h. The time of the first jumping of mice (i.e., latency) and the times of jumping of mice within 5 minutes (i.e., errors times) were tested and recorded with jumping apparatus, and the latency and error times were used as the investigation indexes of the experiment.

5. Statistic Analysis

All experimental data were expressed as $\bar{x}\pm s$. The homogeneity test of variance was firstly carried out with variance analysis. F value was calculated. If F value was $<F_{0.05}$, it could be concluded that there was no significant difference among mean values of various groups. If F value$\geq F_{0.05}$ and P$\leq$0.05, statistic analysis was carried out by using the method of pairwise comparison of mean values among a plurality of experimental groups and a control group. Appropriate variable conversion was carried out for data with non-normality or heterogeneity of variance, and the converted data were used for statistic analysis after the requirement of normality or homogeneity of variance was satisfied. If the purpose of normality or homogeneity of variance was still not achieved after conversion, rank sum test was employed instead for statistic analysis.

6. Determination of Results

In accordance with "technical specifications of health food inspection and evaluation" (2003 edition), the effect of the test sample of improving memory was determined according to the following criteria.

The experimental results of the protective effect on memory acquisition had statistically significance.

The experimental results on the protective effect on memory acquisition showed that, compared with the normal control group, the latency of jumping down the platform was significantly shorten in the mice of the model group which was administered with scopolamine hydrobromide (p<0.01), and the error times was significantly increased (p<0.01). Learning performance of each product group was better than the model group, and the latency in the high dosage group was significantly prolonged (p<0.05). The error times in the group of positive control drug Huperzine A was significantly reduced (p<0.05), and the latency was significantly prolonged (p<0.05). The above results suggested that the present product had an obvious improving effect on scopolamine hydrobromide induced memory acquired disorders in mice, see Table 8.

TABLE 8

Effect on the scopolamine hydrobromide induced memory acquired disorder in mice ($\bar{X} \pm s$).

| Groups | Dosage (/kg) | n | Latency (s) | Error times |
|---|---|---|---|---|
| Normal control group | | 12 | 208.26 ± 69.07 | 0.76 ± 0.76 |
| Model group | | 12 | 66.18 ± 4246$^\Delta$ | 2.54 ± 1.91$^\Delta$ |
| Low dosage group | 1.3 g | 12 | 119.50 ± 87.62 | 1.80 ± 1.21 |
| High dosage group | 2.6 g | 12 | 138.50 ± 96.45* | 1.30 ± 1.20 |
| Huperzine A | 0.1 mg | 12 | 146.20 ± 99.97* | 1.00 ± 0.82* |

Note:
Compared with the normal control group, $^\Delta$p < 0.01, $^{\Delta\Delta}$p < 0.01;
compared with the model group, * p < 0.05, **p < 0.01.

In this example, use of the animal model of memory lapse not only helped to assess the effect of medicaments, but also could preliminarily analyze their mechanism of action. Scopolamine is M cholinergic receptor antagonist, which can block the M cholinergic receptor in cerebral cortex, septal area and hippocampus, causing cholinergic system dysfunction, thereby resulting in decline of learning and memory abilities. This experiment also proved that scopolamine could significantly reduce the learning and memory abilities in mice. The latency of jumping down the platform of mice was significantly shortened in the model group administered with 5 mg/kg scopolamine hydrobromide (p<0.01), and the error times was increased significantly (p<0.01). However, administration of a certain dosage of the product samples of the present invention had a significant improving effect on scopolamine hydrobromide induced memory acquired disorder in mice.

In accordance with "technical specifications of health food inspection and evaluation" (2003 edition), the conclusion drawn from this animal study was that the test sample had the effect of memory improvement.

The above description are only preferred embodiments of the present invention. It should be noted that several improvements and modifications can also be made by those ordinary skilled in the art without departing from the principles of the present invention, and these improvements and modifications should also fall within the scope of the present invention.

The invention claimed is:

1. A memory improving composition, which is made from materials consisting of 200-800 parts of Arillus Longan, 200-800 parts of Semen Nelumbinis, 200-800 parts of Poria, 10-150 parts of enzymatic extract of Semen Juglandis, 10-150 parts of phosphatidylserine, and 3-50 parts of taurine, wherein the enzymatic extract of Semen Juglandis is a hydrolysate of Semen Juglandis dregs after hydrolyzation with alkaline endoprotease Alcalase™ (*Bacillus* protease preparation) 2.4L and complex protease Protamex™ (*Bacillus* protease preparation);

wherein the enzymatic extract of Semen Juglandis is prepared by the following method:
(a) grinding Semen Juglandis dregs in water to obtain a slurry of Semen Juglandis dregs, adding alkali to adjust the pH value to 8.0 to 9.0, centrifuging, removing impurities in the supernatant enzymatically, adding acid to cause precipitation, washing the precipitate to obtain a walnut protein;
(b) hydrolyzing the walnut protein to a hydrolysis degree of 8-12% with alkaline endoprotease Alcalase™ 2.4L and complex protease Protamex™, and collecting the supernatant as enzymatic hydrolysate of walnut protein after enzyme deactivation and centrifugation;

(c) enriching enzymatic extract of Semen Juglandis by separating the enzymatic hydrolysate of walnut protein through a filter cloth and ultrafiltration membrane.

2. The composition according to claim 1, which is prepared by extracting Arillus Longan, Poria and Semen Nelumbinis by water decoction, and mixing with enzymatic extract of Semen Juglandis, phosphatidylserine and taurine.

3. The composition according to claim 1, wherein removing impurities in the supernatant enzymatically in the step (a) is carried out by adding 1% of α-amylase and 0.5% of cellulase relative to the total weight of the Semen Juglandis dregs to the supernatant.

4. The composition according to claim 1, wherein the step (b) is carried out as follows:

stirring the walnut protein with addition of water, adding alkaline endoprotease Alcalase™ 2.4L in an amount of 2000-3000 U/g protein and complex protease Protamex™ in an amount of 1200-2500 U/g protein, hydrolyzing to a hydrolysis degree of 8-12% at 50-55° C., and collecting the supernatant after enzyme deactivation and centrifugation to obtain the enzymatic hydrolysate of walnut protein.

5. The composition according to claim 1, wherein the step (c) is carried out as follows:

filtering the enzymatic hydrolysate of walnut protein through a 100 mesh filter cloth, then through an ultrafiltration membrane with a membrane flux of 10000 Da, producing a permeation liquid, then filtering the permeation liquid through an ultrafiltration membrane with a membrane flux of 1000 Da, collecting a retentate to obtain a walnut polypeptide solution, concentrating under vacuum to achieve a solid content of 30-40% and spray drying to obtain the enzymatic extract of Semen Juglandis.

* * * * *

UNITED STATES PATENT AND TRADEMARK OFFICE
CERTIFICATE OF CORRECTION

PATENT NO. : 10,376,552 B2
APPLICATION NO. : 15/252528
DATED : August 13, 2019
INVENTOR(S) : Yong Zhou et al.

It is certified that error appears in the above-identified patent and that said Letters Patent is hereby corrected as shown below:

On the Title Page

Item (71) Applicant, delete the entirety of the item and replace with --INFINITUS (CHINA) COMPANY LTD., Jiang Men City (CN)-- therefor.

Item (72) Inventors, delete the entirety of the items and replace with --Yong Zhou, Jiang Men City (CN); Xiaolei Guo, Jiang Men City (CN); Chung Wah Ma, Jiang Men City (CN)-- therefor.

Item (73) Assignee, delete the entirety of the item and replace with --INFINITUS (CHINA) COMPANY LTD., Jiang Men City, (CN)-- therefor.

Signed and Sealed this
Eighth Day of October, 2019

Andrei Iancu
*Director of the United States Patent and Trademark Office*